United States Patent [19]

Jones et al.

[11] Patent Number: 5,352,761

[45] Date of Patent: Oct. 4, 1994

[54] NAPHTHALENE DICARBOXYLIC ACIDS AND ESTERS SUBSTITUTED WITH AROYL GROUPS

[75] Inventors: Allan S. Jones, Church Hill; Charles E. Sumner, Jr., Kingsport, both of Tenn.

[73] Assignee: Eastman Chemical Company, Kingsport, Tenn.

[21] Appl. No.: 160,766

[22] Filed: Dec. 3, 1993

[51] Int. Cl.$^5$ ............................................. C08G 63/189
[52] U.S. Cl. ................................. 528/298; 568/308; 568/335; 568/336; 528/220; 528/272; 528/299; 528/302; 528/308
[58] Field of Search ................. 568/308, 335, 336; 528/220, 272, 298, 299, 302, 308

[56] References Cited

PUBLICATIONS

CA105 (22): 192805x.
CA98 (25): 214870f.
Chen Shangxian et al., "Fluorescence Spectra of Poly(Ethylene-2,6-Naphthalene Dicarboxylate)", *Scientia Sinica,* vol. XXIV, No. 5, May 1981.
Cao Ti et al., "Intermolecular Excimer Interaction in Poly(Polytetramethylene Ether Glycol Aryl Dicarboxylate", *Acta Chimica Sinica,* vol. 42 No. 1, 1984.

*Primary Examiner*—Samuel A. Acquah
*Attorney, Agent, or Firm*—John D. Thallemer

[57] ABSTRACT

This invention relates to naphthalene dicarboxylic acids or naphthalene dicarboxylic esters substituted with aroyl groups. More particularly, this invention relates to the following compounds: dialkyl 1-benzoyl-2,6-naphthalene dicarboxylate, 7-C1-C$_8$-alkoxycarbonyl-1-C1-Cs-alkoxy-l-aryl(1,3-H$_2$ naphtho {1,2-c} furan-3-ones), and dialkyl 1-(2-naphthoyl)-2,6-naphthalene dicarboxylate. The compounds are useful in any polymer composition where dicarboxylic acids or dicarboxylic esters are used especially in poly(ethylene 2,6-naphthalene dicarboxylate) compositions where reduced fluorescence is desired.

5 Claims, No Drawings

NAPHTHALENE DICARBOXYLIC ACIDS AND ESTERS SUBSTITUTED WITH AROYL GROUPS

FIELD OF THE INVENTION

This invention relates to naphthalene dicarboxylic acids or naphthalene dicarboxylic esters substituted with aroyl groups. More particularly, this invention relates to the following compounds: dialkyl 1-benzoyl-2,6-naphthalene dicarboxylate, 7-$C_1$-$C_8$-alkoxycarbonyl-1-$C_1$-$C_8$-alkoxy-1-aryl(1,3-$H_2$ naphtho {1,2-c}furan-3-ones), and dialkyl 1-(2-naphthoyl)-2,6-naphthalene dicarboxylate. The compounds are useful in any polymer composition where dicarboxylic acids or dicarboxylic esters are used especially in poly(ethylene 2,6-naphthalene dicarboxylate) compositions where reduced fluorescence is desired.

BACKGROUND OF THE INVENTION

It is well known that dicarboxylic acids and dicarboxylic esters are reacted with glycols to prepare polyesters. Polyesters are used in the fabrication of various articles for household or industrial use, including appliance parts, containers, and auto parts. One major drawback of many polyesters, however, are their inherent bluish fluorescence. Articles prepared with polyesters such as poly(ethylene 2,6-naphthalene dicarboxylate) (PEN) have a hazy and bluish appearance. This phenomenon is especially of concern in the packaging of foods and beverages wherein the food or beverage inside the PEN container appears unnatural.

Fluorescence is a type of luminescence in which an atom or molecule emits radiation in passing from a higher to a lower electronic state. The term is restricted to phenomena in which the time interval between absorption and emission of energy is extremely short ($10^{-10}$ to $10^{-6}$ second). Fluorescence in a polymer or small molecule, occurs when a photon is emitted from an excited singlet state. Quenching of fluorescence eliminates or reduces the ability for photon emission by providing an alternative pathway for the excited state energy such as vibronic or heat loss, or intersystem crossing to the excited triplet state.

Methods to quench fluorescence in PEN have been disclosed by Chen Shangxian et al. in an article entitled, "Fluorescence Spectra Of Poly(Ethylene-2,6-Naphthalene Dicarboxylate)" which appeared in *SCIENTIA SINICA*, Vol. XXIV, No. 5, May 1981, and by CAO Ti et al. in an article entitled, "Intermolecular Excimer Interaction In Poly(Polytetramethylene Ether Glycol Aryl Dicarboxylate)" which appeared in *ACTA CHIMICA SINICA*, Vol. 42, No. 1, 1984. Both of the references disclose the use of o-chlorophenol to quench PEN fluorescence in a chloroform solution. Dissolving the PEN in a chloroform solution to disperse the fluorescence quencher therein, however, is not practical on an industrial scale because only very dilute PEN solutions can be prepared. In addition, the PEN must have a low molecular weight to dissolve in the chloroform solution.

In contrast, the present inventors have unexpectedly determined that incorporation of 0.1 to 5 mole percent of a naphthalene dicarboxylic acid or naphthalene dicarboxylic ester substituted with an aroyl group(s) in PEN significantly reduces fluorescence without deleteriously affecting the physical properties of the polyester.

SUMMARY OF THE INVENTION

Accordingly, it is one object of the present invention to provide naphthalene dicarboxylic acids or naphthalene dicarboxylic esters substituted with aroyl groups.

Accordingly, it is another object of the present invention to provide 7-$C_1$-$C_8$-alkoxycarbonyl-1-$C_1$-$C_8$-alkoxy-1-aryl(1,3-$H_2$ naphtho (1,2-c)furan-3-ones) and these compounds incorporated in poly(ethylene-2,6-naphthalene dicarboxylate) compositions to reduce fluorescence.

These and other objects are accomplished herein by a naphthalene dicarboxylic acid or naphthalene dicarboxylic ester substituted with aroyl groups which reduces fluorescence in polyester compositions having a formulae selected from the group consisting of

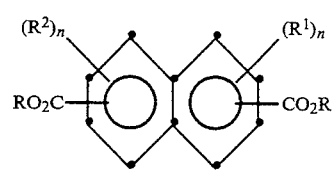

and

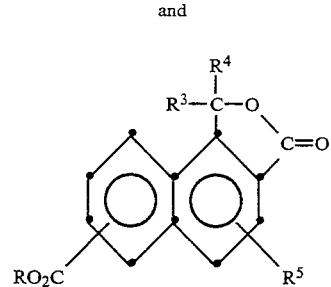

wherein R is independently selected from the group consisting of hydrogen, $C_1$-$C_8$ alkyl, substituted $C_1$-$C_8$ alkyl, $C_3$-$C_8$ alkenyl, $C_3$-$C_8$ cyclo alkyl and aryl; $R^1$ and $R^2$ are independently selected from the group consisting of hydrogen, halogen, $C_1$-$C_8$ alkyl, aryl and tolyl, and an aroyl group having $C_6$-$C_{12}$ carbon atoms; and n is an integer of 1 to 3; provided that $R^1$ or $R^2$ is an aroyl group; $R^3$ is a $C_1$-$C_8$ alkoxy group; $R^4$ is an aryl group; $R^5$ is independently selected from the group consisting of hydrogen and halogen.

DESCRIPTION OF THE INVENTION

The present invention relates to naphthalene dicarboxylic acids or naphthalene dicarboxylic esters substituted with aroyl groups and 7-$C_1$-$C_8$ alkoxycarbonyl-1-$C_1$-$C_8$ alkoxy-1-aryl (1,3-$H_2$ naphtho{1,2-c}furan-3-ones), exemplified by 7-MeOOC-1-MeO-1-phenyl-(1,3-H2-naphtho[1,2-c]furan-3-one). Examples of naphthalene dicarboxylic acids or naphthalene dicarboxylic esters substituted with aroyl groups include: dialkyl aroyl-2,6-naphthalene dicarboxylate, such as dimethyl 1-benzoyl-2,6-naphthalene dicarboxylate, and dialkyl 1-(2-naphthoyl)-2,6-naphthalene dicarboxylate, such as dimethyl 1-(2-naphthoyl)-2,6-naphthalene dicarboxylate.

Dimethyl 1-benzoyl-2,6-naphthalene dicarboxylate has the formula:

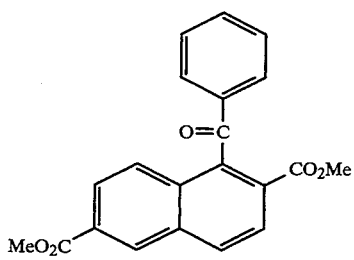

Dimethyl 1-(2-naphthoyl)-2,6-naphthalene dicarboxylate has the formula:

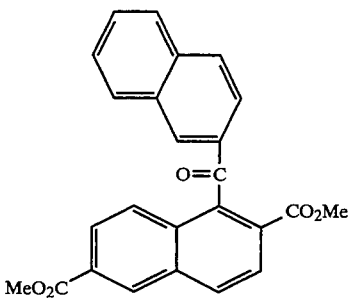

7-MeOOC-1-MeO-1-Ph-(1,3-H$_2$-naphtho{1,2-c}furan-3-one) has the formula:

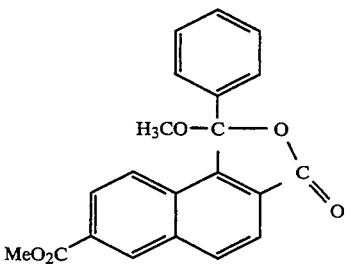

In the above definitions, the term "$C_1$–$C_8$ alkyl" is used to designate a straight or branched chain saturated hydrocarbon radical having the specified number of carbon atoms.

The term "substituted $C_1$–$C_8$ alkyl" is used to designate an alkyl radical containing one to three groups, preferably one group, selected from hydroxy, $C_1$–$C_8$ alkoxy, phenyl, $C_3$–$C_8$ alkenyl or $C_3$–$C_8$ cycloalkyl.

In the term "$C_1$–$C_8$ alkoxy", the alkyl portion of the radical is a straight or branched chain saturated hydrocarbon radical attached to oxygen.

The terms "aryl" and "aroyl" are used to designate aromatic hydrocarbon radicals containing 6–12 carbon atoms and the radicals attached to carbonyl, respectively. The aryl portion of the groups may be substituted with one to three substitutes selected from $C_1$–$C_8$ alkyl, $C_1$–$C_8$ alkoxy or halogen.

The term "$C_3$–$C_8$ alkenyl" is used to denote aliphatic hydrocarbon moieties having 3–8 carbons and containing at least one carbon-carbon double bond.

The term "$C_3$–$C_8$ cycloalkyl" is used to designate a cycloaliphatic hydrocarbon radical containing the specific number of carbons.

The term "halogen" is used to indicate bromine, chlorine, fluorine and iodine.

In the term "$C_1$–$C_8$ alkoxy carbonyl", the alkyl portion of the radical is a straight or branched chain saturated hydrocarbon radical.

The naphthalene dicarboxylic acids or naphthalene dicarboxylic esters substituted with aroyl groups and the substituted 1,3-H$_2$ naphtho[1,2-c]furan-2-ones are prepared by processes such as those disclosed in the examples. It is important to note that in the processes, aqueous sodium dichromate is the preferred oxidizing agent for oxidizing ketone substituted naphthalene rings. The oxidation of polyaromatic rings by oxidizing agents such as potassium permanganate, chromic acid, and nitric acid may result in ring degradation.

The naphthalene dicarboxylic acids or naphthalene dicarboxylic esters substituted with an aroyl group may be combined with one or more dicarboxylic acids and diols to form a polyester or copolyester. The term "polyester" as used herein shall include copolyesters. The polyesters are usually based on 100 mole percent dicarboxylic acid and 100 mole percent diol.

Alternatively, the naphthalene dicarboxylic acids or naphthalene dicarboxylic esters substituted with an aroyl group may be added to a polyester such as PEN in an amount of 0.1 to 5 mole percent, preferably 0.5 to 2 mole percent. The naphthalene dicarboxylic acids or naphthalene dicarboxylic esters substituted with an aroyl group act as fluorescence quenching compounds in polyester compositions. Using more than 5 mole percent, however, hinders the crystallization of the polyester and results in inferior physical properties. The fluorescence quenching compounds may be copolymerized or melt blended with the polyester.

Suitable dicarboxylic acids or esters thereof that may be used with the naphthalene dicarboxylic acids or naphthalene dicarboxylic esters substituted with an aroyl group include aromatic dicarboxylic acids preferably having 8 to 14 carbon atoms, aliphatic dicarboxylic acids preferably having 4 to 12 carbon atoms, or cycloaliphatic dicarboxylic acids preferably having 8 to 12 carbon atoms. Examples of dicarboxylic acids which may be included with the above-mentioned dicarboxylic acids are: terephthalic acid, phthalic acid, isophthalic acid, naphthalene-2,6dicarboxylic acid, cyclohexanedicarboxylic acid, cyclohexanediacetic acid, diphenyl-4,4'-dicarboxylic acid, succinic acid, glutaric acid, adipic acid, azelaic acid, sebacic acid, and the like.

It should be understood that use of the corresponding acid anhydrides, esters, and acid chlorides of these acids is included in the term "dicarboxylic acid".

Diols to be used in the polyester include cycloaliphatic diols preferably having 6 to 20 carbon atoms or aliphatic diols preferably having 2 to 20 carbon atoms. Examples of such diols are: ethylene glycol, diethylene glycol, triethylene glycol, 1,4-cyclohexanedimethanol, propane-1,3-diol, butane-1,4-diol, pentane-1,5-diol, hexane-1,6-diol, 3-methylpentanediol-(2,4), 2-methylpentanediol-(1,4), 2,2,4-trimethylpentane-diol-(1,3), 2-ethylhexanediol-(1,3), 2,2-diethylpropane-diol-(1,3), hexanediol-(1,3), 1,4-di-(hydroxyethoxy)-benzene, 2,2-bis-(4-hydroxycyclohexyl)-propane, 2,4-dihydroxy-1,1,3,3-tetramethyl-cyclobutane, 2,2-bis-(3-hydroxyethoxyphenyl)-propane, and 2,2-bis-(4-hydroxypropoxyphenyl)-propane. Polyesters may be prepared from one or more of the above diols.

The polyester resin may also contain small amounts of trifunctional or tetrafunctional comonomers such as trimellitic anhydride, trimethylolpropane, pyromellitic dianhydride, pentaerythritol, and other polyester forming polyacids or polyols generally known in the art.

The polyester is prepared by conventional polycondensation procedures well-known in the art which generally include a combination of melt phase and solid state polymerization. Melt phase describes the molten state of the polyester or copolyester during the initial polymerization process. The initial polymerization process includes direct condensation of the dicarboxylic acid(s) with the diol(s) or by ester interchange using the ester of the dicarboxylic acid(s). For example, the naphthalene dicarboxylic acids or naphthalene dicarboxylic esters substituted with an aroyl group are ester interchanged with the diol(s) at elevated temperatures in the presence of a catalyst. The melt phase is concluded by extruding the polymer into strands and pelletizing. The polymer may optionally be solid stated. Solid stating involves heating the polymer pellets to a temperature in excess of 200° C., but well below the crystalline melt point, either in the presence of an inert gas stream or in a vacuum to remove a diol. Several hours are generally required in the "solid state" unit to build the molecular weight to the target level.

Typical polyesterification catalysts which may be used include titanium alkoxides, dibutyl tin dilaurate, combinations of zinc, manganese, or magnesium acetates or benzoates with antimony oxide or antimony triacetate.

Additives such as fillers, for example, titanium dioxide and talc, stabilizers, antioxidants, buffers, colorants, dyes, pigments and the like normally used with polymers may be used if desired. Such additives, their amounts, and their use are well known in the art.

The polyester products of this invention are readily melt processed into useful shapes and forms. For example, they may be melt pressed or extruded into films, extruded into rods or other shapes, injection molded or compression molded into various objects, and injected molded preforms may be reheated and blown into bottles, jars and the like.

The materials and testing procedures used for the results shown herein are as follows:

Glass transition temperature (Tg), melting temperature (Tm) and crystallization half-time ($t_{\frac{1}{2}}$) were determined by differential scanning calorimetry (DSC) using a Perkin-Elmer DSC II instrument. The Tg and Tm were determined using a 20° C./minute scan rate after the samples had been heated above the Tm and quenched below the Tg. The $t_{\frac{1}{2}}$ was determined by the following method: The sample was heated to 300° C. under a nitrogen atmosphere and held for two minutes. The sample was removed from the DSC and immediately cooled to −20° C. The DSC was cooled to 50° C. and the sample was returned to the DSC. The temperature of the DSC was increased at a rate of 320° C./minute to a test temperature of 190° C., 210° C. or 230° C. Samples were isothermally crystallized at each of the test temperatures. The crystallization half-time ($t_{\frac{1}{2}}$) is the time required to reach the peak on the crystallization exotherm.

Inherent viscosity (I.V.) was measured at 23° C. using 0.50 grams of polymer per 100 ml of a solvent consisting of 60% by weight phenol and 40% by weight tetrachloroethane.

The present invention will be further illustrated by a consideration of the following examples, which are intended to be exemplary of the invention. All parts and percentages in the examples are on a weight basis unless otherwise stated.

EXAMPLE 1

1-benzoyl-2,6dimethylnaphthalene was prepared by the following procedure.

2,6-dimethyl naphthalene (100 grams, 0.64 moles), aluminum chloride (89.3 grams, 0.67 moles), carbon disulfide (600 mL), and methylene chloride (200 mL) were added to a 3-neck 2L flask fitted with a mechanical stirrer and cooled to 0°–5° C. Benzoyl chloride (94.2 grams, 0.67 moles) was added dropwise over a period of about 1 hour. The temperature was maintained below 10° C. during the addition and throughout the reaction. The reaction mixture was stirred for 6 hours and then decomposed by pouring into ice/HCl. The organic layer was washed 5 times with water and then dried for 12 hours over sodium sulfate. The organic layer was concentrated to a viscous oil and treated with methanol, precipitating 1-benzoyl-2,6-dimethylnaphthalene as an off-white solid. The 1-benzoyl-2,6-dimethylnaphthalene was collected and dried (105 grams, 63%).

The 1-benzoyl-2,6-dimethylnaphthalene was determined to be pure by gas chromatography with a melting point of 81°–82° C. (literature mp 84C). A molecular weight of 260 was confirmed by Field Desorption Mass Spectroscopy (FDMS).

EXAMPLE 2

The 1-benzoyl-2,6-dimethylnaphthalene prepared in Example 1 was oxidized to 1-benzoyl-2,6-naphthalenedicarboxylic acid by the following procedure.

1-benzoyl-2,6-dimethylnaphthalene (60 grams, 0.23 moles), sodium dichromate (185 grams, 0.621 moles), and 500 mL water were added to a one liter high pressure autoclave and purged with nitrogen. The high pressure oxidation was carried out for 6 hours at 250° C. with stirring. Chromium oxide was filtered off and the liltrate was acidified with $HC_1$ resulting in precipitation of 1-benzoyl-2,6-naphthalenedicarboxylic acid as a light yellow material (67 grams, 90% yield) which was used on the next step without further purification. The 1-benzoyl-2,6-naphthalenedicarboxylic acid had a melting point over 315° C. and FDMS confirmed molecular weight of 320.

EXAMPLE 3

The 1-benzoyl-2,6-naphthalenedicarboxylic acid prepared in Example 2 was converted to its dimethyl ester, dimethyl 1-benzoyl-2,6-naphthalene dicarboxylate, by the following procedure.

1-benzoyl-2,6-naphthalenedicarboxylic acid (100 grams, 0.313 moles) and methanol (600 mL) were added to a one liter high pressure autoclave fitted with a magnetic stirrer. The autoclave was purged with nitrogen. High pressure esterification was carried out for 2 hours at 250° C. with stirring. The reaction mixture was concentrated to dryness which resulted in a light brown solid. Recrystallization from methanol followed by three treatments with activated carbon in acetone resulted in (upon concentration) 75 grams (69%) of almost white dimethyl 1-benzoyl-2,6-naphthalene dicarboxylate.

The dimethyl 1-benzoyl-2,6-naphthalene dicarboxylate had a melting point of 135°–137° C. and was determined to be pure by gas chromatography. FDMS confirmed a molecular weight of 348 and the 1H-NMR and $^{13}$C-NMR spectra were consistent with the stated structure. Elemental analysis was also consistent with the stated structure. Found: C 72.22% (calc. 72.41 for $C_{21}H_{16}O_5$); H 4.55% (calc. 4.63)

EXAMPLE 4

Preparation of 7-MeOOC-1-MeO-1-Ph- (1,3-$H_2$-naphtho [1,2-c]furan-3-one) from 1-benzoyl-2,6-naphthalenedicarboxylic acid.

1-benzoyl-2,6-naphthalenedicarboxylic acid (2.9 grams, 0.0091 moles), toluene (75 mL), pyridine (1 drop), and thionyl chloride (10 mL) were added to a 100 mL 3-neck flask with stirring. After 1.5 hrs at reflux, the solution became homogeneous. The solution was allowed to reflux for 30 minutes before methanol (20 mL) was slowly added and then the solution was refluxed for another hour. After cooling, the solution was concentrated to dryness. Recrystallization from methanol afforded 1.5 grams of dark orange product. Column chromatography (methylene chloride, SiO2) and concentration to dryness yielded 0.65 g of the above compound.

The 7-MeOOC-1-MeO-1-Ph-(1,3-H2-naphtho{1,2-c}furan-3-one) was GC pure and had a melting point of 150°–153° C. FDMS confirmed a molecular weight of 348 and the 1H-NMR and 13C-NMR spectra were consistent with the stated structure. Elemental analysis was also consistent with the stated structure. Found: C 72.61% (calc. 72.41 for $C_{21}H_{16}O_5$); H 4.65% (calc. 4.63)

EXAMPLE 5

1-(2-naphthoyl)-2,6-dimethylnaphthalene was prepared by the following procedure.

Dimethyl-2,6-naphthalene dicarboxylate (39.0 grams, 0.25 moles), aluminum chloride (34.6 grams, 0.26 moles), carbon disulfide (220 mL), and methylene chloride (75 mL) were added to a 1L 3-neck flask fitted with a mechanical stirrer and cooled to 0°–5° C. 2-naphthoyl chloride (50.0 grams, 0.26 moles) was added dropwise over a period of about 1 hour. The temperature was maintained below 5° C. during the addition of 2-naphthoyl chloride and throughout the reaction. The reaction mixture was stirred for 4.5 hours and then decomposed by pouring into ice/HCl The organic layer was washed five times with water and then dried for 12 hours over sodium sulfate. The organic layer was concentrated to a viscous oil and treated with methanol, precipitating 1-(2-naphthoyl)-2,6-dimethylnaphthalene which appeared as an off-white solid. The 1-(2-naphthoyl)-2,6-dimethylnaphthalene was collected and dried (66.3 grams, 85.4%).

The 1-(2-naphthoyl)-2,6-dimethylnaphthalene had a melting point of 100°–103° C. Field Desorption Mass Spectroscopy (FDMS) confirmed the molecular weight of 310 g/mole.

EXAMPLE 6

The 1-(2-naphthoyl)-2,6-dimethylnaphthalene prepared in Example 5 was oxidized to 1-(2-naphthoyl)-2,6-naphthalenedicarboxylic acid by the following procedure.

1-(2-naphthoyl)-2,6-dimethylnaphthalene (30.0 grams, 0.097 moles), sodium dichromate (77.9 grams, 0.26 moles), and 300 mL water were added to a 0.5 liter high pressure autoclave and purged with nitrogen. The high pressure oxidation was carried out for 6 hours at 250° C. with stirring. Chromium oxide was filtered off and the filtrate was acidified with $HC_1$ resulting in precipitation of 1-(2-naphthoyl)-2,6-naphthalenedicarboxylic acid as a light yellow material (25.8 grams, 72% yield) which was used on the next step without further purification. The 1-(2-naphthoyl)-2,6-naphthalenedicarboxylic acid had a melting point over 320° C. and FDMS confirmed molecular weight of 370.

EXAMPLE 7

The 1-(2-naphthoyl)-2,6-naphthalenedicarboxylic acid prepared in Example 6 was converted to its dimethyl ester, dimethyl 1-(2-naphthoyl)-2,6-naphthalene dicarboxylate by the following procedure.

1-(2-naphthoyl)-2,6-naphthalenedicarboxylic acid (25.0 grams, 0.068 moles) and methanol (300 mL) were added to a 0.5 liter high pressure autoclave fitted with a magnetic stirrer. The autoclave was purged with nitrogen. High pressure esterification was carried out for 2 hours at 250° C. with stirring. The reaction mixture was concentrated to dryness which resulted in a light brown solid. Recrystallization from a mixture of methanol (1000 mL) and methylene choride (200 mL) resulted in 16.5 grams of orange brown solid. The solid was dissolved in methylene chloride (500 mL) and was treated with activated carbon (three times). Crystallization was accomplished by concentrating to 80 mL of solution and adding methanol (300 mL). A white solid, 13.0 grams, 48% yield, of dimethyl 1-(2-naphthoyl)-2,6-naphthalene dicarboxylate was collected by filtration.

The dimethyl 1-(2-naphthoyl)-2,6-naphthalene dicarboxylate had a melting point of 186°–188° C. and was determined to be pure by gas chromatography. FDMS confirmed a molecular weight of 398 and the $^1$H-NMR and $^{13}$C-NMR spectra were consistent with the stated structure. Elemental analysis was also consistent with the stated structure. Found: C 74.93% (calc. 75.37 for $C_{25}H_{18}O_5$); H 4.55% (calc. 4.55)

EXAMPLE 8

Poly(ethylene 2,6-naphthalene dicarboxylate) was prepared by the following procedure.

Dimethyl 2,6-naphthalene dicarboxylate (0.5 moles, 122 grams), ethylene glycol (1.0 moles, 62 grams), and catalyst metals were placed in a 500 mL polymerization reactor under a nitrogen atmosphere. The mixture was heated with stirring at 200° C. for 2 hours. The temperature was increased to 220° C. and maintained for 1 hour. The temperature was increased to 290° C. which took approximately 20 minutes. When the temperature reached 290° C., the nitrogen flow was stopped and vacuum was applied. The polymer was stirred under vacuum (0.1–0.3 mm Hg) for 50 minutes. The polymer was cooled and ground. The florescence intensity and I.V. of the polymer are summarized in Table I, and Tg, Tm and $t_{\frac{1}{2}}$ are listed in Table II.

EXAMPLE 9

Poly(ethylene 2,6-naphthalene dicarboxylate) with 0.5 mole percent copolymerized dimethyl 1-benzoyl-2,6-naphthalene dicarboxylate from Example 3, was prepared by the following procedure.

Dimethyl 2,6-naphthalene dicarboxylate (0.124 moles, 30.35 grams), dimethyl 1-benzoyl-2,6-naphthalene dicarboxylate (0.00063 moles, 0.22 grams), ethylene glycol (0.25 moles, 15.5 grams), and catalyst metals were placed in a 100 mL polymerization reactor under a nitrogen atmosphere. The polymer was prepared according to the procedure as set forth in Example 1. The florescence intensity and I.V. of the polymer are summarized in Table I, and Tg, Tm and crystallization half-time from the glossy state ($t_{\frac{1}{2}}$) are listed in Table II.

TABLE I

| EXAMPLE | AROMATIC KETONE (mole %) | I.V. (dL/g) | Florescence INTENSITY (at 430 nm) |
|---|---|---|---|
| 1 | PEN control | 0.42 | 100 |
| 2 | PEN + 0.5% 1-benzoyl-DMN[1] | 0.48 | 47 |
| 3 | PEN + 1.0% 1-benzoyl-DMN[1] | 0.47 | 33 |
| 4 | PEN + 2.0% 1-benzoyl-DMN[1] | 0.43 | 26 |
| 5 | PEN + 5.0% 1-benzoyl-DMN[1] | 0.45 | 13 |
| 6 | PEN + 1.2% benzoyl-DMT[2] | 0.38 | 79 |
| 7 | PEN + 2.0% benzoyl-DMT[2] | 0.42 | 62 |
| 8 | PEN + 3.5% benzoyl-DMT[2] | 0.44 | 62 |
| 9 | PEN + 5.0% benzoyl-DMT[2] | 0.39 | 43 |
| 10 | PEN + 0.5% 1-(2-naphthoyl)-N[3] | 0.35 | 40 |
| 11 | PEN + 1.0% 1-(2-naphthoyl)-N[3] | 0.39 | 28 |

[1]dimethyl 1-benzoyl-2,6-naphthalene dicarboxylate
[2]dimethyl benzoylterephthalate
[3]1-(2-naphthoyl)-2,6-naphthalene dicarboxylate The results in Table I clearly indicate that the poly(ethylene-2,6-naphthalene dicarboxylate) compositions containing a critical amount of an aromatic ketone as a florescence quencher, which is copolymerized in the PEN backbone, exhibit significantly less florescence than PEN compositions without the florescence quencher. In addition, the data in Table I also indicates that the use of the florescence quencher in a critical amount does not deleteriously affect the inherent viscosity of the polyester.

TABLE II

| EXAMPLE | AROMATIC KETONE (mole %) | Tg (°C.) | Tm (°C.) | $t_{\frac{1}{2}}$ (min.) 190° C. | 210° C. | 230° C. |
|---|---|---|---|---|---|---|
| 1 | PEN control | 123 | 268 | 2.5 | 1.5 | 2.5 |
| 2 | PEN + 0.5% 1-benzoyl-DMN[1] | — | — | 5.7 | 3.7 | 5.8 |
| 3 | PEN + 1.0% 1-benzoyl-DMN[1] | — | — | 6.0 | 4.2 | 7.9 |
| 4 | PEN + 2.0% 1-benzoyl-DMN[1] | 123 | 262 | — | — | — |
| 5 | PEN + 5.0% 1-benzoyl-DMN[1] | 126 | — | — | — | — |
| 6 | PEN + 1.2% benzoyl-DMT[2] | — | — | 3.0 | 1.9 | 3.1 |
| 7 | PEN + 2.0% benzoyl-DMT[2] | — | — | 3.9 | 2.6 | 4.9 |
| 8 | PEN + 3.5% benzoyl-DMT[2] | — | — | 3.8 | 2.8 | 6.3 |
| 9 | PEN + 5.0% benzoyl-DMT[2] | — | — | 4.0 | 3.3 | 8.8 |
| 10 | PEN + 0.5% 1-(2-naphthoyl)-N[3] | 122 | 266 | — | — | — |
| 11 | PEN + 1.0% 1-(2-naphthoyl)-N[3] | 124 | 266 | — | — | — |

[1]dimethyl 1-benzoyl-2,6-naphthalene dicarboxylate
[2]dimethyl benzoylterephthalate
[3]1-(2-naphthoyl)-2,6-naphthalene dicarboxylate The results in Table II establishes the critical range for the aromatic ketones as florescence quenchers which are copolymerized in the poly(ethylene-2,6-naphthalene dicarboxylate) backbone. The data indicates that 0.1 to 5 mole percent of the aromatic ketones reduce florescence without deleteriously affecting the physical properties of the polyester. In contrast, greater than 5 mole percent of the aromatic ketones in the compositions slows down the crystallization rate to an unacceptable level.

Many variations will suggest themselves to those skilled in this art in light of the above detailed description. All such obvious modifications are within the full intended scope of the appended claims.

What is claimed is:

1. A substituted 1,3-H$_2$ naphtho{1,2-c}furan-3-one compound having the formula:

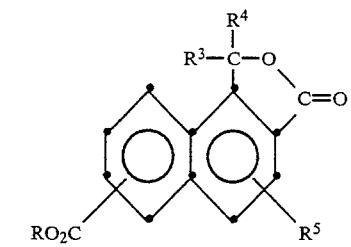

wherein R is independently selected from the group consisting of hydrogen, $C_1$–$C_8$ alkyl, substituted $C_1$–$C_8$ alkyl, $C_3$–$C_8$ alkoxy group; $R^4$ is an aryl group; $R^5$ is independently selected from the group consisting of hydrogen and halogen.

2. The dimethyl 1-(2-naphthoyl)-2,6-naphthalene dicarboxylate according to claim 1 having the formula:

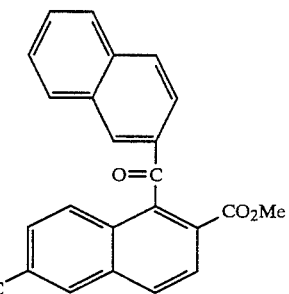

3. The 7-MeOOC-1-MeO-1Ph-(1,3-H$_2$-naphtho{1,2-c}furan-3-one) according to claim 1 having the formula:

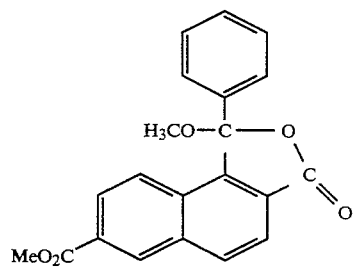

4. A poly(ethylene 2,6-naphthalene dicarboxylate) composition with reduced fluorescence comprising repeat units from:

(a) a dicarboxylic acid component which comprises at least 85 mole percent of a dicarboxylic acid selected from the group consisting of naphthalene-2,6-dicarboxylic acid, and naphthalene-2,6-dicarboxylate ester;

(b) a diol component which comprises at least 85 mole percent of ethylene glycol; and (c) 0.1 to 5 mole percent, based on 100 mole percent dicarboxylic acid and 100 mole percent diol, of one or more substituted 1,3-H$_2$naphtho{1,2-c}furan-3-one compounds having the formula:

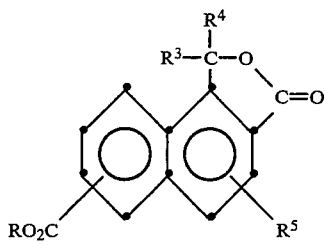

wherein R is independently selected from the group consisting of hydrogen, C$_1$-C$_8$ alkyl, substituted C$_1$-C$_8$ alkyl, C$_3$-C$_8$ alkenyl, C$_3$-C$_8$ cyclo alkyl and aryl; R$^3$ is a C$_1$-C$_8$ alkoxy group; R$^4$ is an aryl group; R$^5$ is independently selected from the group consisting of hydrogen and halogen.

5. A poly(ethylene 2,6-naphthalene dicarboxylate) composition with reduced fluorescence according to claim 8 comprising repeat units from:

(a) a dicarboxylic acid component which comprises at least 85 mole percent of a dicarboxylic acid selected from the group consisting of naphthalene-2,6icarboxylic acid, and naphthalene-2,6icarboxylate ester;

(b) a diol component which comprises at least 85 mole percent of ethylene glycol; and (c) 0.3 to 2.5 mole percent, based on 100 mole percent dicarboxylic acid and 100 mole percent diol, of one or more substituted 1,3-H$_2$naphtho[1,2-c]furan-3-one compounds having the formula:

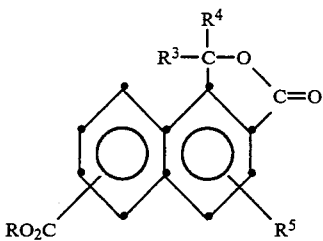

wherein R is independently selected from the group consisting of hydrogen, C$_1$-C$_8$ alkyl, substituted C$_1$-C$_8$ alkyl, C$_3$-C$_8$ alkenyl, C$_3$-C$_8$ cyclo alkyl and aryl; R$^3$ is a C$_1$-C$_8$ alkoxy group; R$^4$ is an aryl group; R$^5$ is independently selected from the group consisting of hydrogen and halogen.

* * * * *

UNITED STATES PATENT AND TRADEMARK OFFICE
CERTIFICATE OF CORRECTION

PATENT NO. : 5,352,761
DATED : October 4, 1994
INVENTOR(S) : Allan S. Jones et al It is certified that error appears in the above-indentified patent and that said Letters Patent is hereby corrected as shown below:

Column 10, line 13 (Claim 1), between "$C_3-C_8$" and "alkoxy", ---alkenyl, $C_3-C_8$ cyclo alkyl and aryl; $R^3$ is a $C_1-C_8$ --- should be inserted.

Column 12, line 3 (Claim 5), "8" should be ---4---.

Column 12, line 7 (Claim 5), "2,bicarboxylic" should be ---2-dicarboxylic---.

Column 12, line 7 (Claim 5), "2,bicarboxy-" should be ---2-dicarboxy- ---.

Signed and Sealed this

Twenty-fourth Day of January, 1995

BRUCE LEHMAN

Attest:

Attesting Officer

Commissioner of Patents and Trademarks